United States Patent [19]

Mills et al.

[11] Patent Number: 4,829,091

[45] Date of Patent: May 9, 1989

[54] PROCESS FOR THE PREPARATION OF KETONES AND NOVEL INSECTICIDES PRODUCED THEREFROM

[75] Inventors: Frank D. Mills, Highland; Richard T. Brown, Silver Spring; Jr. Mills, Laurel, all of Md.

[73] Assignee: The United States of America as represented by the Secretary of Agriculture, Washington, D.C.

[21] Appl. No.: 55,265

[22] Filed: May 27, 1987

[51] Int. Cl.$^4$ ............................................. A61K 31/12
[52] U.S. Cl. .................................. 514/684; 568/325; 568/329; 568/330; 568/314; 560/53; 549/501; 549/498; 514/679; 514/683; 514/461; 514/530; 514/531
[58] Field of Search ................. 568/325, 329, 330; 514/683, 684; 71/123

[56] References Cited

U.S. PATENT DOCUMENTS

| | | | |
|---|---|---|---|
| 4,206,230 | 6/1980 | Paul | 71/121 |
| 4,218,468 | 8/1980 | Paul | 71/121 |
| 4,713,392 | 12/1987 | Elliott et al. | 568/329 |

OTHER PUBLICATIONS

A. Paul Krapcho et al., "Decarbalkoxylations of Geminal Diesters, β-Keto Esters and α-Cyano Esters Effected by Sodium Chloride in Dimethyl Sulfoxide," Tetrahedron Letters 12: 957–960 (1973).

P. E. Berteau et al., "Pyrethroid-Like Biological Activity of Compounds Lacking Cyclopropane and Ester Groupings," Science 161: 1151–1153 (1968).

D. H. Hunter et al., "Synthetic Applications of Crown Ethers; The Malonic Ester Synthesis," Synthesis, pp. 37–39 (1977).

A. Paul Krapcho, "Synthetic Applications of Dealkoxycarbonylations of Malonate Esters, β-Keto Esters, α-Cyano Esters and Related Compounds in Dipolar Aprotic Media–Part I," Synthesis pp. 805–822 (1982).

*Primary Examiner*—James H. Reamer
*Attorney, Agent, or Firm*—David Sadowski; M. Howard Silverstein

[57] ABSTRACT

An improved method for the decarbalkoxylation of alkylated β-keto esters to obtain high yields of ketones. In accordane with the method, decarbalkoxylation of alkylated β-keto esters is accomplished by heating the esters in the presence of dilute aqueous alkali and an effective amount of a phase-transfer agent. The method produces commercially practical yields of ketone in a manner which is facile, economical and environmentally safe. Novel methylene-linked pyrethroid ketones produced from the improved method exhibit insecticidal activity against various agricultural pests.

4 Claims, No Drawings

PROCESS FOR THE PREPARATION OF KETONES AND NOVEL INSECTICIDES PRODUCED THEREFROM

BACKGROUND OF THE INVENTION

1. Field of the Invention

The present invention relates to an improved method for converting β-keto esters to ketones, and to novel ketones produced therefrom. Specifically, this invention relates to the method of decarbalkoxylating alkylated β-keto esters using a phase-transfer agent to yield ketones. The present invention also relates to novel methylene-linked pyrethroid insecticides produced by the method of the invention.

2. Description of the Prior Art

Ketones are very valuable commercial compounds. One synthetic route for the preparation of ketones is via the conversion of alkylated β-keto esters. Classical synthetic approaches to such conversions are known. For example, it is known that acid-catalyzed decarboxylation in an aqueous or nonaqueous medium, following alkaline hydrolysis of β-keto esters provides simple access to ketones. However, because this conversion method can be unpredictable, with little or no yield, its use as a commercial synthetic process is not desirable.

Several previous and more recent approaches to ketone synthesis through conversion of β-keto esters employ a retro Claisen-type reaction. Such syntheses require a nonaqueous medium and/or high reaction temperatures, thereby presenting a potential environmental hazard and necessitating much time and expense. Also, the retro Claisen-type reactions are undesirable since they may require another method to complete the synthesis. For example, when a crown ester is used to convert several β-sp$^2$ carbon ester compounds to carboxylates in an alkaline medium, acidification and/or thermolysis are required to complete ketone synthesis.

Consequently, there exists a need for a method of converting alkylated β-keto esters to ketones which is more predictable, cost effective, and environmentally safer than prior art processes. In addition, there is a need for a facile approach to the conversion of β-keto esters to ketones which produces a yield which is practical for commercial application.

SUMMARY OF THE INVENTION

It is an object of the present invention to provide an improved process for the decarbalkoxylation of alkylated β-keto esters to produce high yields of ketones.

Another object of the present invention is to provide a novel process for the conversion of the β-keto esters to ketones in a facile, economical and commercially acceptable manner.

Still another object of the present invention is to provide novel methylene-linked pyrethroid insecticidal compounds.

In accordance with the method of the invention, decarbalkoxylation of β-keto esters is accomplished by heating the ester in the presence of dilute aqueous alkali and an effective amount of a phase-transfer agent for a period of time sufficient to decarbalkoxylate the ester. An advantageous feature of the invention method is that the process is not specific, but may be used to prepare a limitless quantity of keto products.

Examples of novel methylene-linked pyrethroid insecticides produced by the method of the invention include compounds represented by the general formula

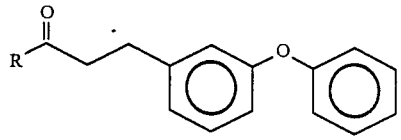

wherein R is 2,2-dimethyl-3-(2-methylpropenyl)cyclopropyl; 2,2-dimethyl-3-(cyclopentanylidenemethyl)cyclopropyl; or 1-(4-chlorophenyl)-2-methyl propyl. Other novel methylene-linked pyrethroid insecticides produced by the invention method include compounds represented by the general formula

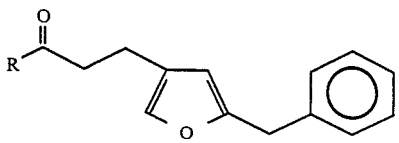

wherein R is 2,2-dimethyl-3-(cyclopentanylidenemethyl)cyclopropyl; or 2,2-dimethyl-3-(2,2-dichlorovinyl)cyclopropyl.

DETAILED DESCRIPTION OF THE INVENTION

For purposes of this invention, the term "phase-transfer agent" is defined herein to mean a reagent that allows the transport of a reactive species between two immiscible phrases.

In the preferred embodiment, the method comprises (1) forming an emulsion of a β-keto ester with dilute aqueous alkali, i.e. potassium hydroxide or sodium hydroxide, which contains an effective amount, preferably from about 0.1 to 10%, of a phase-transfer agent such as hexadecycltrimethylammonium bromide, cetyltrimethylammonium bromide, benzylcetyldimethylammonium chloride, or the like; (2) heating said emulsion at about 60° C. to 90° C., perferably under nitrogen, with stirring and sonication for about a period of time sufficient to decarbalkoxylate the ester, preferably from about 30 to 90 minutes; (3) neutralizing the reaction mixture with dilute acid, i.e. dilute sulfuric or hydrochloric acid; and (4) thereafter, recovering the resulting ketone.

To aid emulsion formation, the β-keto ester may optionally be dissolved in an organic solvent such as toluene, hexane or heptane, prior to mixing with the dilute alkali solution containing the phase-transfer agent. Preferred reaction times and temperatures for individual esters may vary depending upon the molecular weight of the esters. It appears that the lower the molecular weight of the ester, the lower the temperature and the shorter the reaction time required to complete decarbalkoxylation.

Isolation of the ketone is accomplished by extraction of the crude reacton mixture with an appropriate organic solvent, e.g. ethyl ether, ethyl acetate or the like. The crude product is sequentially washed with dilute base and saturated salt solutions. Thereafter, the crude product is dried over a suitable drying agent, filtered and the solvent removed. Final purification may be accomplished by dry-packed silica gel, column chromatography using an appropriate organic solvent.

3

It is within the scope of this invention to prepare the esters using any suitable esterification procedure. In general, the β-keto esters useful in the invention method may be synthesized from their acid chloride using the well-known Meldrum's acid (2,2-dimethyl-1,3-dioxane-4,6-dione). The resulting trione is thereafter converted to the desired β-keto ester with the appropriate alcohol. Alternatively, the esters may be prepared by condensing the precursor ketone, which is obtained using the cadmium methyl alkylation of the corresponding acid chloride with diethyl carbonate.

Alkylation of the formed β-keto ester may be accomplished using conventional alkylation methodology. For example, the esters may be alkylated with the appropriate alkyl halide in the presence of a suitable base, or with sodium hydride in an appropriate solvent, i.e. THF or benzene.

Products prepared from the ketones produced from the method of the invention have a variety of commercial uses including, but not limited to, perfumed, flavor additives, antioxidants, preservatives, inhibitors, intermediates for resins, plastics, adhesives, pharmaceuticals and dyes. Some ketone products such as methylene-linked pyrethroids have demonstrated insecticidal activity.

When used, the ketones produced by the method of the invention may be used in solid or liquid form. As will be obvious to one skilled in the arts, the ketones may be used in various compositions of ketones and a carrier. Depending upon the intended use, such compositions may additionally contain conventional additives such as emulsifying agents, wetting agents, binding agents, odorants, stabilizers and the like.

The following examples are intended to further illustrate the invention as herein disclosed and not to limit the scope of the invention as defined by the claims.

EXAMPLE I

Five alkylated β-keto esters having the general formula

wherein $R^1$ is methyl and $R^2$ is propyl, butyl, hexyl, phenylmethyl or phenylethyl, were converted to the corresponding ketones using the phase-transfer decarbalkoxylation method of the invention.

The phase-transfer decarbalkoxylation procedure was as follows: 100 mg of the candidate β-keto ester was added to 5 ml of 10% aqueous potassium hydroxide that contained 0.1% of hexadecyltrimethylammonium bromide. If needed, the ester was dissolved in toluene (100 mg/0.25 ml) to aid micelle formation. The mixture was vigorously stirred under nitrogen and sonication, and heated at 80° C. for 45 minutes. Thereafter, the reaction mixture was acidified with 1N sulfuric acid and the mixture extracted with 25 ml of ethyl ether. The organic phase was dried with MgSO4, filtered and concentrated to a light oil. The isolate was purified by dry column chromatography on silica gel using hexane to develop the column. The isolate was quantified and the structure was confirmed by capillary GC/CI-MS (Extrel Corp., Model EL-400-2 fitted with and EL-1000 data system). Yields of the corresponding ketones are recorded in Table I. In all examples, the yield of the ketones exceeded 75%.

EXAMPLE II

In this example, five alkylated β-keto esters, having the general formula

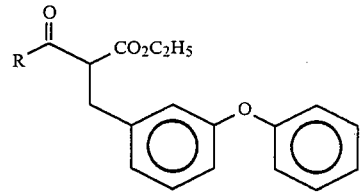

wherein R is 2,2-dimethyl-3-(2-methylpropenyl)cyclopropyl; 2,2-dimethyl 3-(cyclopentanylidenemethyl)cyclopropyl; or 1-(4-chlorophenyl)-2-methyl propyl; and the general formula

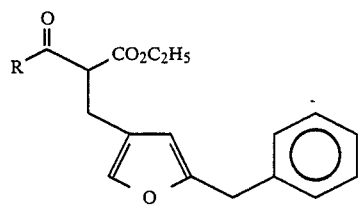

wherein R is 2,2-dimethyl-3-(cyclopentanylidenemethyl)cyclopropyl; or 2,2-dimethyl-3-(2,2-dichlorovinyl)cyclopropyl, were converted to the corresponding methylene-linked pyrethroids using the method of the invention.

TABLE I

| Phase Transfer Catalyzed Decarbalkoxylation of β-Keto Esters ($R^1COCHR^2CO_2C_2H_5$) | | | |
|---|---|---|---|
| β-Keto Ester | | | |
| $R^1$ | $R^2$ | Product | Yield (%)[a,b] |
| Me | $CH_3CH_2CH_2$ | 2-hexanone | 75[c] |
| Me | $CH_3(CH_2)_3$ | 2-heptanone | 85[d] |
| Me | $CH_3(CH_2)_5$ | 2-nonanone | 95[d] |
| Me | $C_6H_5CH_2$ | 1-phenyl-2-butanone | 96[d] |
| Me | $C_6H_5CH_2CH_2$ | 1-phenyl-2-pentanone | 90[d] |

[a]Quadrex 007 Methylsilicone, 15 M × 0.25 mm; flow = 1.7 cm sec$^{-1}$.
[b]Yields of isolated 2-heptanone and 1-phenyl-2-butanone were comparable to those suggested by GLC analyses.
[c]Temp. program: 35° C. for 1 min., 60° C./min. to 80° C., isothermal at 80° C.
[d]Temp. program: 35° C., 60° C./min. to 80° C., then 60° C./min. to 170° C.

The decarbalkoxylation procedure was as follows: A stock reagent was prepared containing 10% of hexadecyltrimethylammonium bromide dissolved in a solution of 10% aqueous potassium hydroxide. 1 g of the candidate β-keto ester was dissolved in a minimum amount of heptane and was added to 50 ml of the reagent. The reaction mixture was sonicated at 80° C. and monitored by analytical TLC. The reaction was usually completed at 90 minutes. The cooled reaction mixture was acidified with dilute hydrochloric acid and then extracted twice with 25 ml of ethyl acetate. The combined organic extracts were washed with 5% sodium bicarbonate and a saturated sodium chloride solution. After drying with MgSO4, filtration and removal of the solvent, the isolate was purified by dry-packed silica gel column chromatography using ethyl acetate (3–10%) in hexane to develop the column. The resulting ketones, each a mixture of two optical isomers, were obtained as a colorless oil or semi-solid at −4° C. Yields are recorded in Table II.

The novel methylene-linked pyrethroids were all produced in good yield. In all examples the yield exceeded 73%. Accordingly, the method of the invention is useful to convert structurally complicated β-keto esters to ketones in commercially acceptable yields.

The novel methylene-linked pyrethroids of Example II were found to exhibit insecticidal activity useful against various agricultural pests. To show the effectiveness of the novel pyrethroids, the insecticidal activities of the compounds of Example II were compared to the activity of phenothrin. Additionally, the activity of the alkylated β-keto ester precursors of the compounds of Example II were compared to that of phenothrin.

TABLE II

Phase-Transfer Catalyzed Decarbalkoxylation of Alkylated β-Keto Esters ($R^1COCHR^2CO_2C_2H_5$)

| Compound | β-Keto Ester ($R^1COCHR^2CO_2C_2H_5$) | |
| --- | --- | --- |
| | $R^1$ | $R^2$ |
| A | [structure] | [structure] |
| B | [structure] | [structure] |
| C | [structure] | [structure] |
| D | [structure] | [structure] |
| E | [structure] | [structure] |

| Compound | Product | Yield (%) |
| --- | --- | --- |
| A | [structure] | 87 |
| B | [structure] | 84 |
| C | [structure] | 86 |

TABLE II-continued

Phase-Transfer Catalyzed Decarbalkoxylation of Alkylated
β-Keto Esters (R¹COCHR²CO₂C₂H₅)

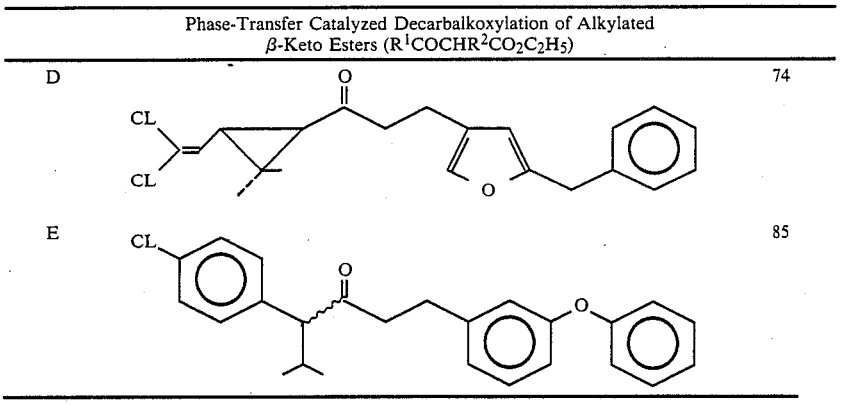

| D | | 74 |
| E | | 85 |

Activity was determined on the basis of results obtained from the foregoing insecticide tests:

INSECTICIDE TEST METHODS

Topical Application Test

Yellow Mealworm, *Tenetrio molitor* Linnaeus (YMW), Method of Treatment

Formulations were made to contain 100 μg of the candidate compound per 1 μl of acetone/DMSO (1:1 volume ratio) solvent. Topical application was performed with 1 μl calibrated glass micropipet fitted with a rubber bulb. One μl of the formulation was applied on the ventral of the last 3 abdominal segments of each of 5 adults, male and female. The insects were placed in a 9 cm petri dish.

Method of Recording Results

Mortality and morbidity were recorded after 72 hours. Mode of action may be by contact.

Feed Additive Test

Fall Armyworm, *Spodoptera frugiperda* (J. E. Smith) (FAW), Method of Treatment

Formulations were prepared to contain 100 μg of the candidate compound per 1 μl of acetone/DMSO (1:1 volume:ratio) solvent. 100 μl of the formulation was incorporated into 100 g of standard hot diet. Treated diets were poured into 1 oz. jelly cups at the rate of 10 g/cup and allowed to cool to room temperature.

Method of Recording Results

First and fifth instars were weighed and mortality was noted after 7 days. Third instars were allowed to go to adult where mortality, egg production and hatch were recorded. Mode of action may be by stomach poison, contact or vapor.

Test concentrations and results are set forth in Table III. Phenothrin used in the above tests was sold under the tradename "Multicide Sumithrin" by McLauglin, Gromley, King Co. of Minneapolis, MN.

As shown in Table III, the newly prepared pyrethroids of Example II showed varied activity against both insect species, YMW and FAW, with activity appearing to be least in the early larval stages. With the exception of compounds A and D, none of the ketones expressed an appreciable antifeedent behavior in larvae FAW. Compound A exhibited some mortality activity in FAW larvae but only compounds D and E had significant mortality. Notably, none of the β-keto esters caused mortality or significant antifeedent activity in the larvae FAW. Looking at the YMW, all the ketones and their alkylated β-keto esters caused 100% mortality in the adult YMW. Only compound D caused 100 percent mortality in the YMW pupae. The remaining compounds were for the most part inactive against the YMW pupae, with only compounds A, B and D¹ showing a minimal activity.

It is understood that modifications and variations may be made to the foregoing disclosure without departing from the spirit and scope of the invention.

TABLE III

Insect Bioassay of Methylene-Linked Pyrethroids[a]
Mortality/Activity at 100 PPM[b]

| Compound | Fall Army Worm (FAW) Larvae[c] (%)[d] | Yellow Meal Worm (YMW) Pupae | Yellow Meal Worm (YMW) Adult |
| --- | --- | --- | --- |
| A¹[e] | 0(71) | 0 | 100 |
| B¹[e] | 0(70) | 0 | 100 |
| C¹[e] | 0(70) | 0 | 100 |
| D¹[e] | 0(80) | 20 | 80 |
| E¹[e] | 0(75) | 0 | 100 |
| A | 30(49) | 20(.6)[f] | 100 |
| B | 0(90) | 20 | 100 |
| C | 0(84) | 0 | 100 |
| D | 80(68) | 100 | 100 |
| E | 50(20) | 0 | 100 |
| PHENOTHRIN | 100(00) | 100 | 100 |

[a]Only trans geometric isomers of the compounds listed were used in the above test.
[b]Topical application.
[c]1st Instar, diet application.
[d]Relative antifeedant activity (% of normal growth).
[e]A¹, B¹, C¹, D¹, and E¹ represents alkylated β-keto esters precursors ketones A, B, C, D and E.
[f]JH rating.

We claim:

1. A compound represented by the general formula

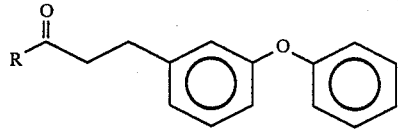

wherein R is 2,2-dimethyl-3-(2-methylpropenyl)cyclopropyl or 2,2-dimethyl-3-(cyclopentanylidenemethyl)cyclopropyl.

2. The compound of claim 1 wherein R is 2,2-dimethyl-3-(2-methyl propenyl)cyclopropyl.

3. The compound of claim 1 wherein R is 2,2-dimethyl-3-(cyclopentanylidenemethyl)cyclopropyl.

4. An insecticidal composition comprising a carrier and an insecticidally effective amount of the compound of claim 1.

* * * * *

UNITED STATES PATENT AND TRADEMARK OFFICE
CERTIFICATE OF CORRECTION

PATENT NO. : 4,829,091

DATED : May 9, 1989

INVENTOR(S) : Frank D. Mills, et al.

It is certified that error appears in the above-identified patent and that said Letters Patent is hereby corrected as shown below:

On the title page, item [75], "Jr. Mills" should read --Giles D. Mills, Jr.--.

Signed and Sealed this

Twentieth Day of February, 1990

*Attest:*

JEFFREY M. SAMUELS

*Attesting Officer*  *Acting Commissioner of Patents and Trademarks*